United States Patent [19]
Bare et al.

[11] Patent Number: 5,665,653
[45] Date of Patent: Sep. 9, 1997

[54] METHOD FOR ENCAPSULATING AN ELECTROCHEMICAL SENSOR

[75] Inventors: Rex O. Bare, Lake Forest; Andy Scherer, San Dimas, both of Calif.

[73] Assignee: Unifet, Incorporated, San Diego, Calif.

[21] Appl. No.: 412,705

[22] Filed: Mar. 29, 1995

[51] Int. Cl.$^6$ .............. H01L 25/04; H01L 25/16; H01L 23/31
[52] U.S. Cl. .............. 438/49; 438/126; 264/272.17
[58] Field of Search .............. 174/52.2, 207; 437/209, 211, 212, 214, 219, 224

[56] References Cited

U.S. PATENT DOCUMENTS

| | | | |
|---|---|---|---|
| 4,233,136 | 11/1980 | Spaziani et al. | 204/195 |
| 4,366,038 | 12/1982 | Kearney et al. | 204/195 |
| 4,496,512 | 1/1985 | Marsoner et al. | 264/267 |
| 4,505,799 | 3/1985 | Baxter . | |
| 4,519,973 | 5/1985 | Cahalan et al. | 264/267 |
| 4,534,825 | 8/1985 | Koning et al. | 437/59 |
| 5,068,205 | 11/1991 | Baxter et al. . | |
| 5,091,341 | 2/1992 | Asada et al. | 437/212 |
| 5,121,289 | 6/1992 | Gagliardi | 361/380 |
| 5,134,773 | 8/1992 | LeMaire et al. | 437/211 |
| 5,139,969 | 8/1992 | Mori | 437/211 |
| 5,147,821 | 9/1992 | McShane et al. | 437/212 |
| 5,179,039 | 1/1993 | Ishida et al. | 437/212 |
| 5,200,362 | 4/1993 | Lin et al. | 437/211 |
| 5,474,958 | 12/1995 | Djennas et al. | 437/212 |
| 5,527,743 | 6/1996 | Variot | 437/212 |
| 5,550,711 | 8/1996 | Burns et al. . | |

FOREIGN PATENT DOCUMENTS

| | | | |
|---|---|---|---|
| 1-164044 | 6/1989 | Japan | 437/212 |

OTHER PUBLICATIONS

Cobben, Peter L.H.M., "Chemically Modified Ion–Sensitive Field–Effect Transistors": Application in Flow–Injection Analysis Cells without Polymeric . . . Analytica Chimica Acta, vol. 248, 1991, pp. 307–313.

Shiono, Satoru, "A Flow—Through Cell for Use with an Enzyme–Modified Field Effect Transistor without Polymeric Encapulation and Wire Bonding", Analytica Chimica Acta, vol. 202, 1987, pp. 131–140.

Primary Examiner—John Niebling
Assistant Examiner—Scott Kirkpatrick
Attorney, Agent, or Firm—Fish & Richardson P.C.

[57] ABSTRACT

An electrochemical sensor assembly which allows a solution to make contact with an active sensing area of a sensor, while constraining the solution such that the fluid does not contact the sensor electronics and a method for fabricating such a sensor assembly. A sensor assembly is fabricated in accordance with a simple process, including: fabricating a master pattern which matches the external profile of an epoxy shell which will encapsulate a substrate upon which the sensors are mounted; forming a flexible tool (or mold) which conforms to the general profile of the master pattern; placing sensors together with any other desired electronic circuitry on a substrate (such as a printed circuit board or a ceramic pad to form a "hybrid"); pressing a number of electrical contact points on the hybrid and the active sensing area of each sensor on the substrate into contact with flexible protrusions of the flexible tool; and potting the hybrid. Due to the fact that the protrusions from the flexible tool are in contact with the hybrid and structures thereon, a seal is formed to prevent potting material from contacting and covering the predetermined areas of the hybrid covered by the protrusions from the flexible tool.

20 Claims, 11 Drawing Sheets

METHOD FOR ENCAPSULATING AN ELECTROCHEMICAL SENSOR

BACKGROUND OF THE INVENTION

1. Field of the Invention

This invention relates to electrochemical sensors for measuring concentration of chemicals in a solution, and more particularly, to an encapsulated electrochemical sensor and a method for encapsulating such a sensor.

2. Description of Related Art

A number of electrochemical sensors are well known in the art. For example, a potassium ion responsive electrode is described in an article by Pioda et al. entitled "Highly Selective Potassium Ion Responsive Liquid-Membrane Electrode", Analytical Letters, vol. 2, pp. 665–674 (1969). Such a sensor is also disclosed in U.S. Pat. No. 3,562,129. In addition, U.S. Pat. No. 3,706,649 (the '649 patent) teaches a substantially solid ion sensitive barrier containing a macrocytic compound, mineral oil, and a lipid which may be used as an ion sensor. Furthermore, a U.K. Patent Application Serial No. 2,025,629 A, published Jan. 23, 1980, discloses an ion selective electrode assembly. Still further, ion-sensitive field-effect transistor (ISFET) sensors are also disclosed in U.S. Pat. No. 4,020,830 to Johnson, et al.

In many solid state sensors, such as ISFET sensors, it is necessary to allow one region of the sensor to come into contact with a solution to be measured, while other regions of the sensor must remain isolated from the solution. This presents a problem in the manufacture of such sensors. One solution to this problem is disclosed in U.S. Pat. No. 4,233,136, issued to Spaziani, et al.

According to Spaziani, a housing having a cover defining a closed interior chamber is fabricated from a rigid plastic material. An interior tubing having a central tubular passage extends axially between firings to create a path for fluid to flow through the assembly. A portion of the wall of the tubing is interrupted by an opening on one side and contains a membrane chemically bonded to, and integral with, the tube. The inner surface of the membrane presents a linear, smooth, continuous surface defining a linear flow path for sample fluids. This configuration allows the solution to contact the membrane in a controlled manner. However, this method is relatively expensive and labor intensive. Furthermore, this method does not easily lend itself to use with ISFETs and other electrochemical sensing devices which do not employ a membrane.

Another method for selectively bringing a solution into contact with the active sensing area of a sensor while confining the solution is presented in an article entitled "A Flow-Through Cell For Use With An Enzyme-Modified Field Effect Transistor Without Polymeric Encapsulation and Wire Bonding" by Satoru Shiono, et al., Analytica Chimica Acta, 202 (1987) 131–140. The article discloses a silicone rubber sheet laid over a silicone substrate on which FETs have been fabricated. The substrate is mounted on a block. Gold lines deposited on the rubber sheet make contact with pads of the FET. A rectangular hole through the silicone rubber sheet allows the solution to contact ion-sensitive portions of the FETs. The substrate is pressed into contact with the silicone rubber sheet. This structure allows a solution to flow past the ion sensitive portions of the FETs without contacting any other portions of the FETs. However, fabricating and assembling the structure disclosed by Shiono is labor intensive, expensive, and has problems with providing good electrical contact and with fluid leakage resulting in poor yield.

Other methods for encapsulating FETs such that a solution to be analyzed is constrained to contact only an active sensing area of the sensor include (1) etching a flow cell, or flow channel, in a rigid epoxy which encapsulates the sensor, and (2) machining flow cells and then manually mounting the sensors in the flow cells. However, both of these methods are time consuming and expensive.

Therefore, there is need for an inexpensive method for fabricating electrochemical sensor assemblies which allow a solution to come into contact only with an active sensing area of sensors while at the same time preventing the fluid from shorting out the sensor electronics. Additionally, in some cases, a reference electrode is required to be in contact with the solution in close proximity to the sensor to maintain a reference voltage. The present invention provides such an inexpensive method and a resulting sensor assembly.

SUMMARY OF THE INVENTION

The present invention is an electrochemical sensor assembly which allows a solution to make contact with an active sensing area of a sensor, while constraining the solution such that the fluid does not contact the sensor electronics. A reference electrode is optionally placed in contact with the solution in close proximity to the sensor to maintain a reference voltage. A method for fabricating such a sensor assembly is also presented.

In accordance with the preferred embodiment of the present invention, a sensor assembly is fabricated in accordance with a simple process. In the first step, a master pattern is fabricated to have a 3-dimensional profile which matches the external profile of an epoxy shell which will encapsulate a substrate upon which the sensors are mounted. The master pattern is placed into a cavity in a rigid tool. Next, the cavity is preferably filled with a liquid substance which is flexible upon curing, such as liquid silicone. Once the poured liquid has cured, the master pattern is removed, leaving a cavity in the flexible tool which conforms to the profile of the master pattern. Sensors, such as ISFETS, are mounted together with any other desired electronic circuitry on a substrate (such as a printed circuit board or a ceramic pad) to form a "hybrid".

In a next step, the hybrid is positioned within the cavity in the flexible tool. Preferably, generally cylindrical protrusions from the inner surfaces of the flexible tool accurately hold the hybrid in position within the cavity in the flexible tool. In accordance with one embodiment of the present invention, an active sensing area on the sensor and a number of electrical contact points on the hybrid are pressed into contact with a protrusion from the inner surface of the cavity in the flexible material. In an alternative embodiment of the present invention, the electrical contacts are connected to wires prior to encapsulation. The open ends of the wires lead outside the cavity to allow an electrical connection to be made with the encapsulated sensor. An additional protrusion from the inner surface of the flexible material is pressed into contact with the active sensing area of each sensor on the substrate. A potting material, such as a liquid epoxy, is then poured, injected or otherwise introduced into the cavity to encapsulate the hybrid. Due to the fact that the protrusions from the flexible tool are in contact with the hybrid and structures thereon (such as the electric contact points and the active regions of the sensors), a seal is formed to prevent potting material from contacting and covering the predetermined areas of the hybrid covered by the protrusions from the flexible tool.

In a next step, once the potting material cures around the hybrid, the potted hybrid is removed from the flexible tool.

In one embodiment, the hybrid is completely encapsulated with the exception of the active sensing area of the sensor. However, in an alternative embodiment in which a flow channel is formed in the potting material that encapsulates the hybrid, a cover or lid is then molded in a second tool. The second tool may be rigid. The lid mates with the potted hybrid to seal a flow channel formed within the potted hybrid. An inlet and an outlet port are molded into the lid such that fluid may flow through a channel in the potting material which encapsulates the hybrid. Finally, if a lid is appropriate, the lid is placed over the potted hybrid to complete the assembly process.

In an alternative process, the flexible material which is formed in the first and second steps is produced by an injection molding process and then placed into a rigid frame which supports the flexible material during the steps of encapsulating the hybrid.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

Figure 1:
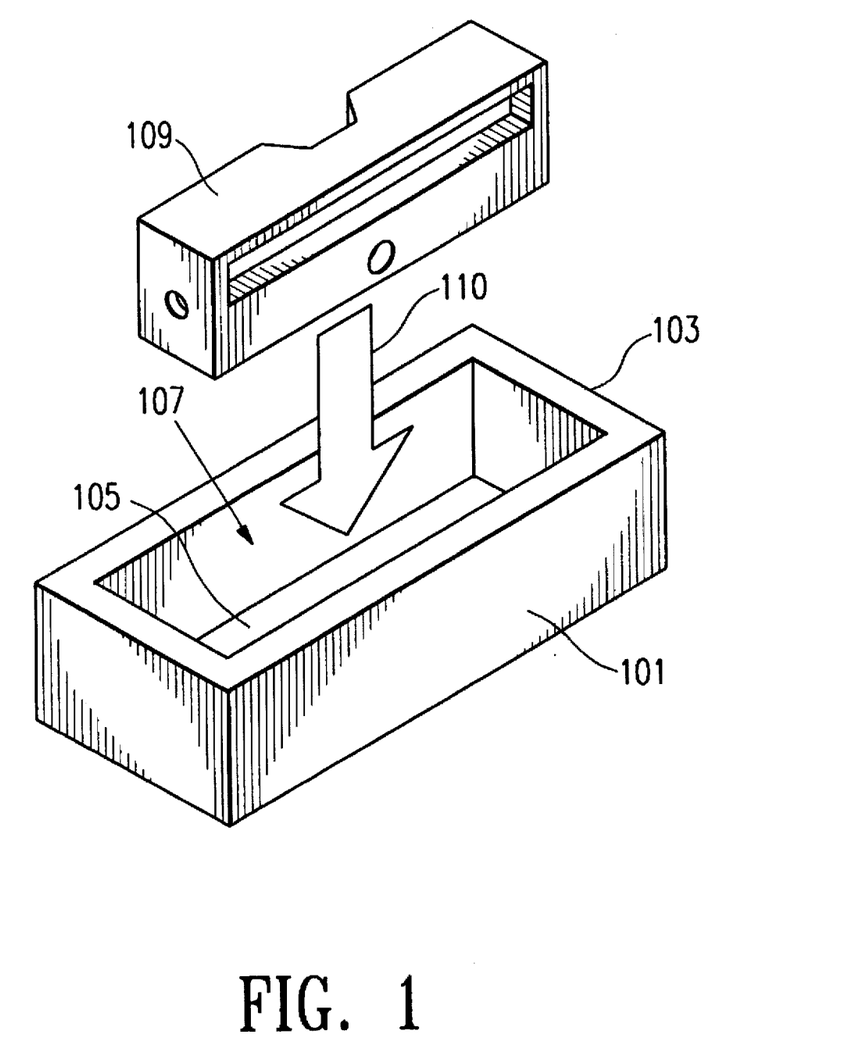
FIG. 1 is a perspective view of a step in a process for encapsulating an electrochemical sensor in accordance with the present invention.
Figure 2A:
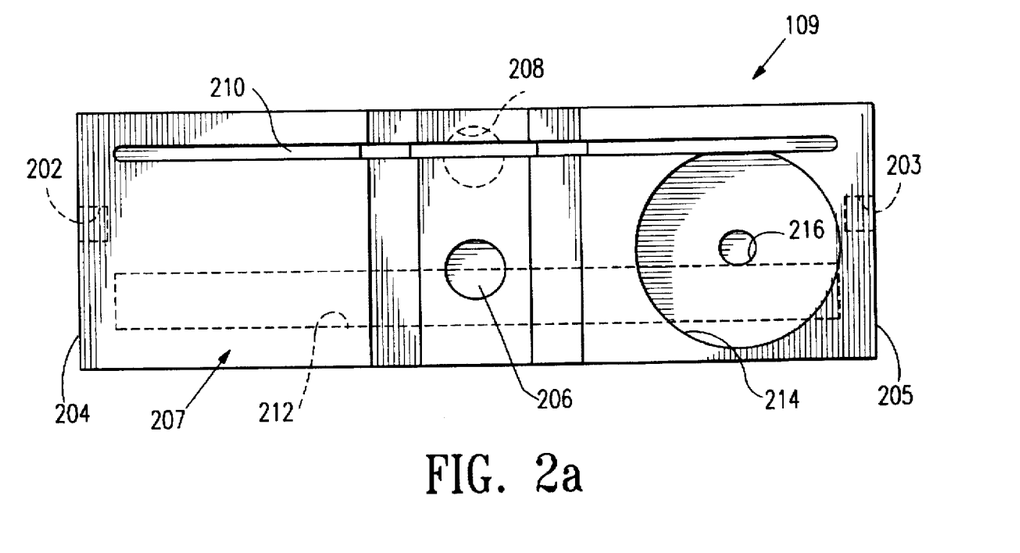
FIG. 2a is a front plan view of a master pattern in accordance with the preferred embodiment of the present invention.
Figure 2B:
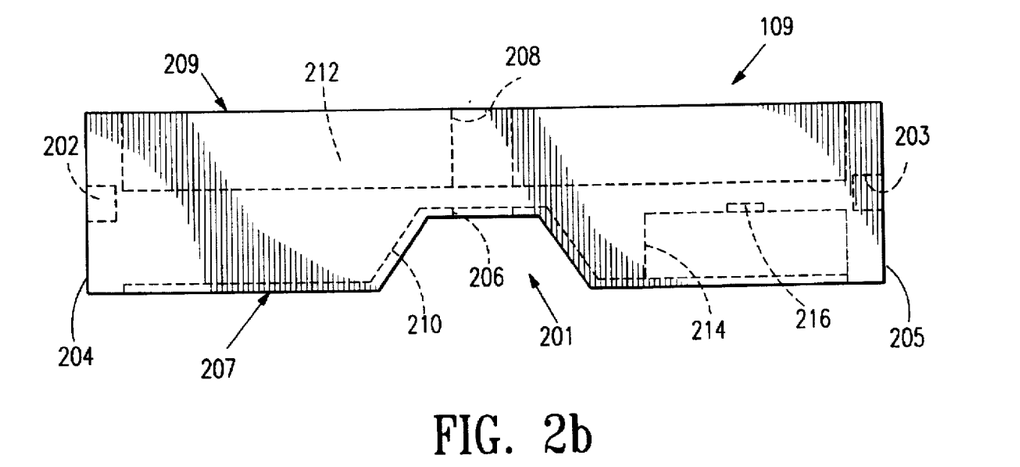
FIG. 2b is a top plan view of the master pattern.

FIG. 1 illustrates the first step in a process for encapsulating an electrochemical sensor in accordance with one embodiment of the present invention. Initially, a master pattern 109 is formed (preferably by machining, and alternatively by any other method, such as laser sintered, or stereo lithography). A preferably essentially rigid tool 101 having four sides 103 and a bottom 105 which form a generally rectangular parallelepiped interior cavity 107 is shown in FIG. 1. In accordance with the first step of the process, the master pattern 109 is placed into the cavity 107 as indicated by an arrow 110. FIG. 2a is a front plan view of a master pattern 109 in accordance with the preferred embodiment of the present invention. FIG. 2b is atop plan view of the master pattern 109. In accordance with one embodiment of the present invention in which a flow channel is to be formed to allow a fluid to flow across the active sensing area of a sensor, a generally U-shaped depression 201 is formed in a front surface 207 of the master pattern 109. Two generally cylindrical side recesses 202, 203 are formed in the sides 204, 205 of the master pattern 109. In addition, a third generally cylindrical recess 206 is formed in the front surface 207 and a fourth generally cylindrical recess 208 is formed in the rear surface 209. A fifth generally cylindrical recess 214 is formed in the front face towards one side 205 of the master pattern 109, and a sixth generally cylindrical recess 216 is formed in the base of the recess 214, the recess 216 having a smaller radius than the recess 214. A narrow channel recess 210 is also provided in the front surface of the master pattern 109. The channel recess 210 is preferably relatively shallow, as can best be seen from the top view shown in FIG. 2b. The channel recess 210 preferably intersects the recess 216, as is best seen in FIG. 2a. A second channel recess 212 having a greater depth than the channel recess 210 is formed in the rear surface 209. The purpose of each of the recesses and channels in the master pattern 109 will be explained below.

Figure 3:
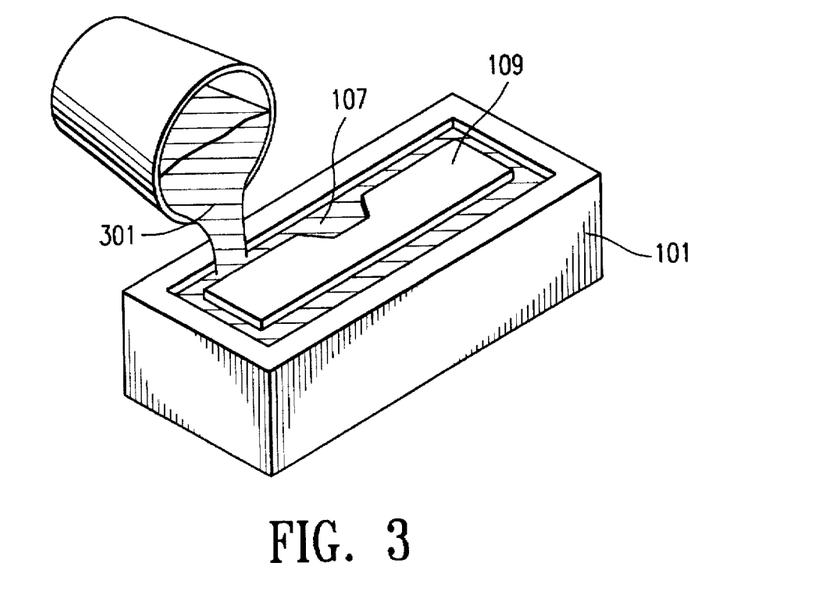
FIG. 3 is a perspective view of another step in the process of fabricating an encapsulated sensor in accordance with the present invention.

FIG. 3 illustrates the second step in the process of fabricating an encapsulated sensor in accordance with one embodiment of the present invention. A curable liquid, such as liquid silicone, 301 which cures to a flexible rubber-like texture, is poured, injected, or otherwise placed into the cavity 107 of the rigid tool 101 and generally conforms to the exterior profile of the master pattern 109 and the interior profile of the walls 103 of the rigid tool 101. When cured, a resulting flexible tool 401 is formed which will retain the reverse shape of the master pattern 109, yet has sufficient elasticity to deform slightly under pressure. It will be understood by those skilled in the art that the present rigid tool 101 may be fashioned in a number of forms, and need not have a generally rectangular parallelepiped interior cavity. That is, the external characteristics of the flexible tool are not critical to the present invention.

In an alternative embodiment, curable liquids, such as vinyls, polyurethanes, rubbers, thermoplastic, elastomers, etc., may be used to fabricate a flexible tool. In another alternative embodiment of the present invention, flexible tools may be inexpensively injection molded in known fashion. Use of a high volume injection molding process allows inexpensive production of large quantities of flexible tools 401. This is very desirable due to the relatively limited life of such flexible tools 401.

Figure 4:
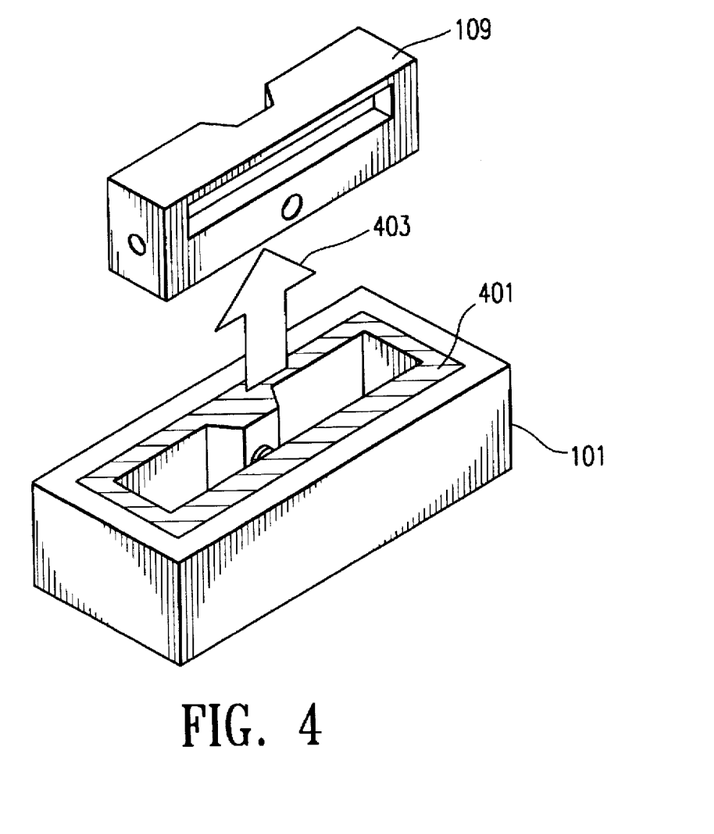
FIG. 4 is a perspective view of another step in the process of fabricating an encapsulated sensor in accordance with the present invention.

FIG. 4 is an illustration of the third step in the process of fabricating an encapsulated sensor in accordance with one embodiment of the present invention. The curable liquid is allowed to cure into the flexible tool 401 and the master pattern 109 is removed from the flexible tool 401, as indicated by an arrow 403 shown in FIG. 4.

Figure 5:
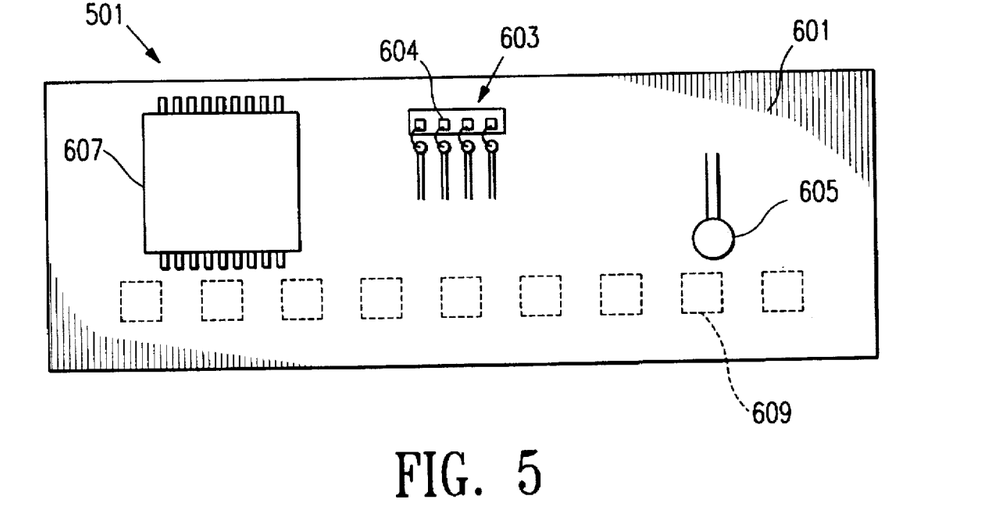
FIG. 5 is a detailed illustration of the from surface of a hybrid in accordance with the present invention.

In accordance with the present invention, a sensor and other circuitry (such as conductive traces and/or electronics) are disposed on a substrate (such as a printed circuit board, ceramic slab, etc.) to form a "hybrid". FIG. 5 is a detailed illustration of the front surface of a hybrid 501. At least one sensor for measuring concentrations of chemicals in fluids (i.e., gas or liquid) (such as an ISFET having a selectively permeable membrane) 603 is attached to the front surface 601 of the substrate. Each sensor 603 has an active sensing area 604 which must be exposed to a fluid (gas or liquid) to be analyzed. In the preferred embodiment of the present invention, the active sensing areas 604 of each sensor 603 are aligned to allow a flow channel to be formed over the active sensing areas 604 in an encapsulating sealant, as will be further explained below. In addition, in one embodiment of the present invention, a reference pad 605 is also provided on the front surface 601 of the hybrid 501. In one embodiment of the present invention, the reference pad 605 is a silver pad. The reference pad 605 establishes a reference electrode. In one embodiment of the present invention, additional electronics, such as an integrated circuit 607, are also mounted on the hybrid 501. The integrated circuit may include an Electronically Erasable Programmable Read Only Memory (EEPROM) for storing calibration information and/or to keep track of the usage of the sensor.

Preferably, on the rear surface of the hybrid 501, a number of contact pads 609 are formed (as shown in dashed lines). The contact pads 609 allow the components of the hybrid 501 to interface with external electronics. The contact pads 609 are preferably formed in a line to allow a single structure on the flexible tool 401 to contact each of the pads 609 and thus seal the pads 609 from the encapsulating potting material, as will further explained below.

Numerous other configurations may be used. For example, the active sensing areas 604 of each sensor 603 may form an are or may be aligned vertically or in any other configuration which allows a single flow channel carrying a solution to pass over each such active sensing area 604 while isolating the solution from portions of the sensor with which contact with the solution would not be desirable. Alternatively, the active sensing areas 604 may be located such that a plurality of flow channels may be formed, each of which are in fluid contact with one another by interconnecting tubes or other channels external to the encapsulated sensor. Likewise, the contact pads 609 may be aligned in any one of a number of configurations. For example, the pads 609 may be grouped in arbitrary groups having one or more pads 609, each such group being sealed by one structure formed on the flexible tool 401, as will be explained in greater detail below.

Figure 6:
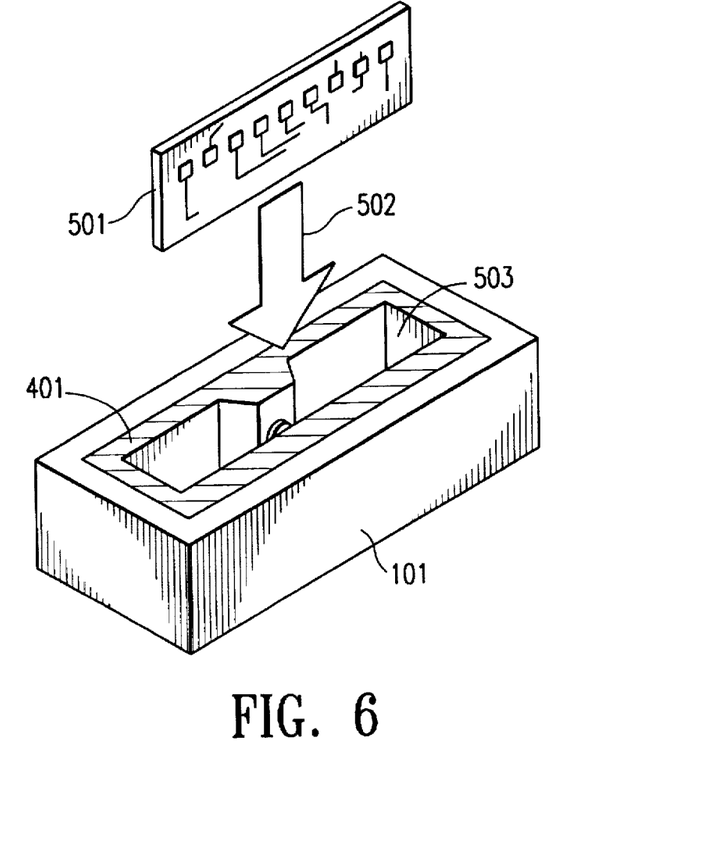
FIG. 6 is a perspective view of another step in the process of fabricating an encapsulated sensor in accordance with the present invention.

FIG. 6 depicts placing the hybrid 501 into the flexible tool 401. An arrow 502 indicates that the hybrid is placed into a cavity 503 in the flexible tool 401. The cavity conforms to the master pattern 109 used to form the flexible tool 401.

Figure 7A:
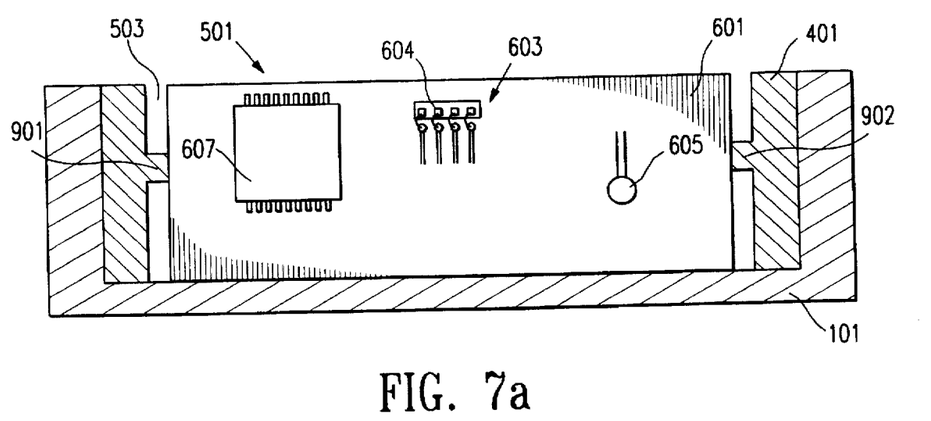
FIG. 7a is a partial cross-sectional view of a hybrid within a cavity in the flexible tool in accordance with the present invention.
Figure 7B:
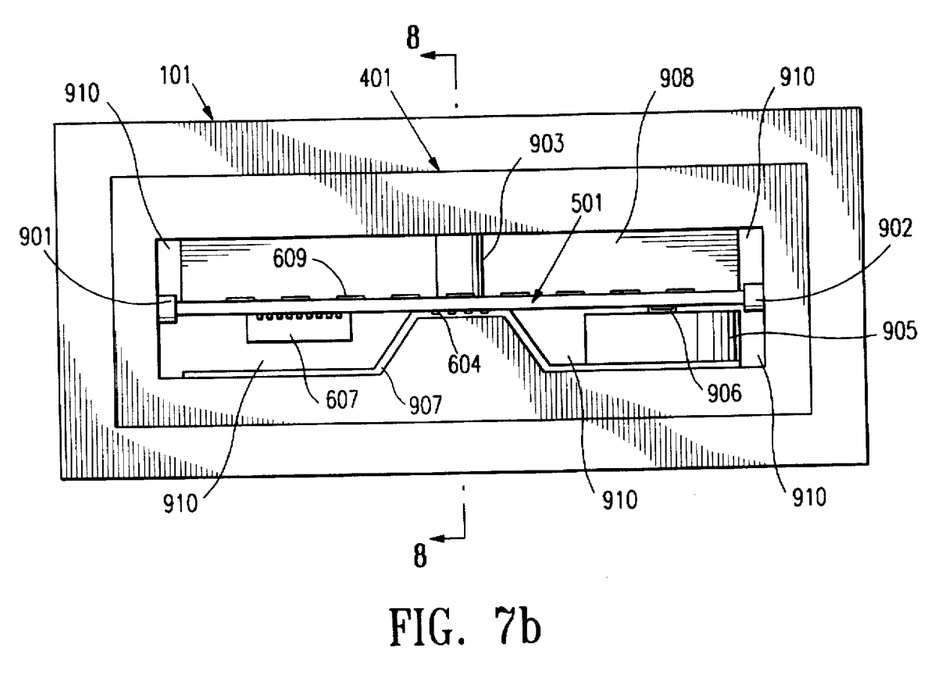
FIG. 7b is a top plan view of the hybrid within the cavity in accordance with the present invention.
Figure 8:
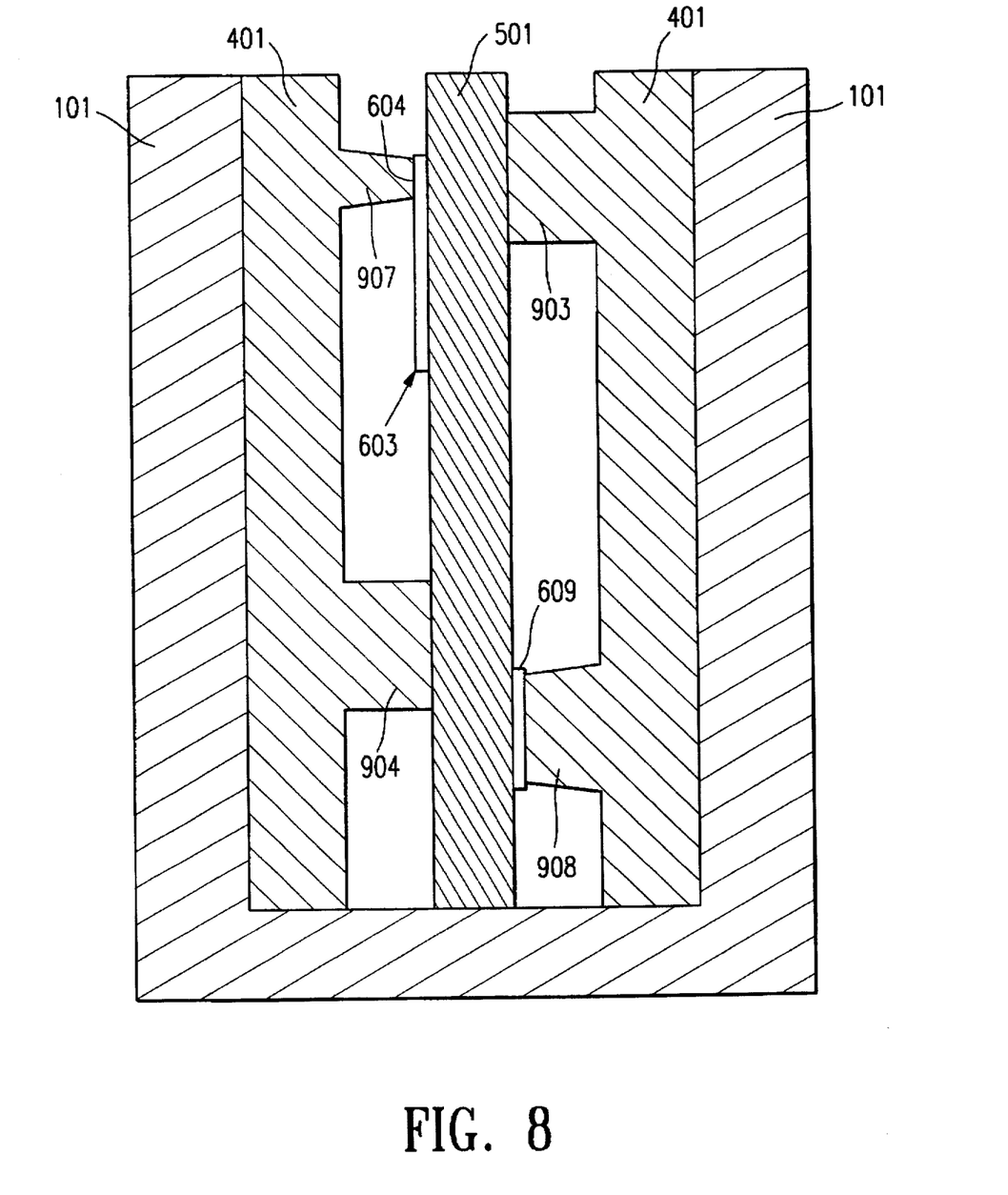
FIG. 8 is a cross-sectional view of the hybrid, the flexible tool, and a rigid tool in accordance with the present invention.

FIG. 7a is a partial cross-sectional view of the hybrid 501 within the cavity 503 in the flexible tool 401. FIG. 7b is a top plan view of the hybrid 501 within the cavity 503. FIG. 8 is a cross-sectional view of the hybrid 501, the flexible tool 401, and the rigid tool 101. In accordance with the embodiment of the present invention depicted in FIGS. 7a and 7b, four generally cylindrical protrusions 901, 902, 903, 904 from the flexible tool 401 provide support for the hybrid 501 within the cavity 503. It will be clear to one of ordinary skill in the art that the particular shape of the protrusions is not essential to the present invention. The protrusion 901 is formed in the flexible tool 401 by the recess 202 in the master pattern 109 (see FIG. 2a and 2b). The protrusion 902 is formed in the flexible tool 401 by the recess 203 in the master pattern 109. The protrusion 903 is formed in the flexible tool 401 by recess 206 in the master pattern 109. The protrusion 904 is formed in the flexible tool 401 by the recess 206 in the master pattern 109. In addition, three generally flexible structures 905, 906, 908 are formed in the flexible tool 401 to seal portions of the hybrid from being encapsulated by a potting material to be introduced in a future step in the process. The structure 905 is a generally cylindrical protrusion formed by the recess 214 in the master pattern 109. The structure 906 is a generally cylindrical protrusion formed by the recess 216 in the master pattern 109. The structure 907 is a narrow protruding ridge which is formed by the narrow recessed channel 210 in the master pattern 109. The structure 908 is a broader protruding ridge which is formed by the broad recessed channel 212 in the master pattern 109.

The hybrid 501 is pressed into contact with the cylindrical protrusion 906. In accordance with the invention as illustrated in FIGS. 7a and 7b in which a reference electrode is provided, the protrusion 906 deforms slightly to form a seal over at least a portion of the reference pad 605 used to form the reference electrode (see FIG. 7a). In similar fashion, the narrow ridge 907 may form a seal over at least a portion of the active sensing areas 604 of the sensors 603 (see FIGS. 6 and 7a) and the broader ridge 908 forms a seal over the pads 609 on the rear surface of the hybrid 501. In the preferred embodiment of the present invention in which an ISFET provided as the sensor 603, the entire active sensing area of the sensor 603 must be exposed if the sensor is to provide accurate information.

Figure 9:
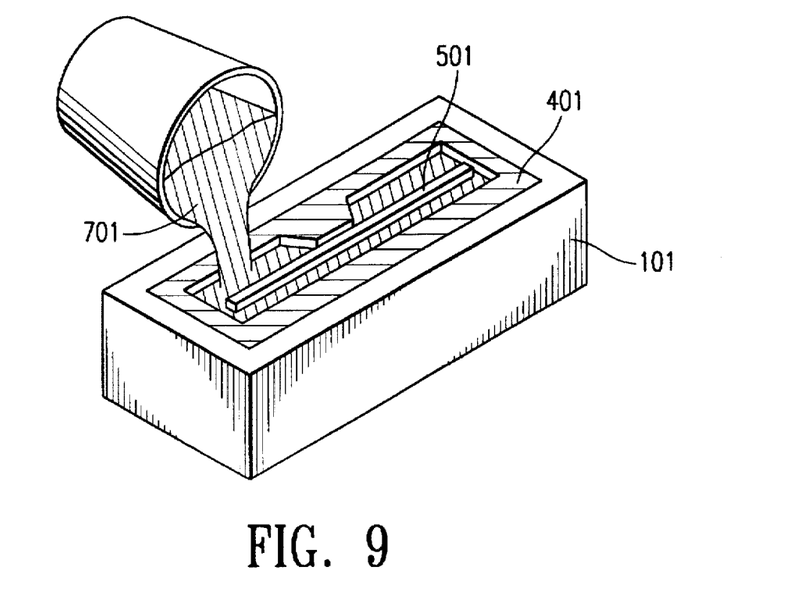
FIG. 9 is a perspective view of another step in the fabrication of an encapsulated sensor in accordance with the present invention.

FIG. 9 illustrates the fifth step in the fabrication of an encapsulated sensor in accordance with one embodiment of the present invention. A curable liquid potting material 701, such as an epoxy resin, is poured or actively drawn into the flexible tool 401 and fills the void 910 between the hybrid 501 and the flexible tool 401.

Figure 10:
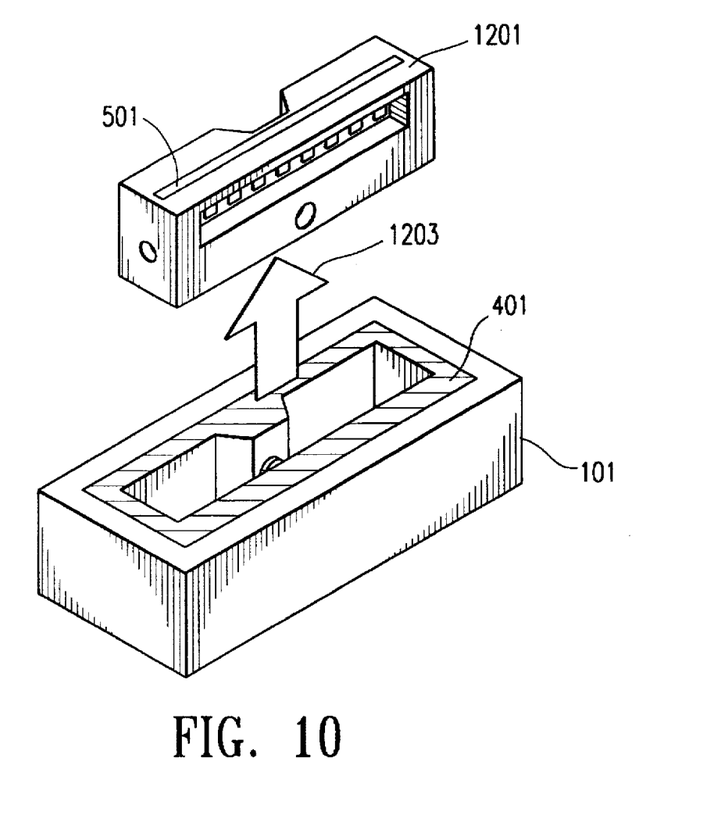
FIG. 10 is a perspective view of another step in the fabrication of an encapsulated sensor in accordance with the present invention.

FIG. 10 illustrates the sixth step in the fabrication of an encapsulated sensor in accordance with one embodiment of the present invention. The potted hybrid 1201 is removed from the flexible tool 401, as indicated by an arrow 1203. In the preferred embodiment of the present invention, the flexible tool 401 is capable of being re-used to form a plurality of potted hybrids 1201.

Figure 11A:
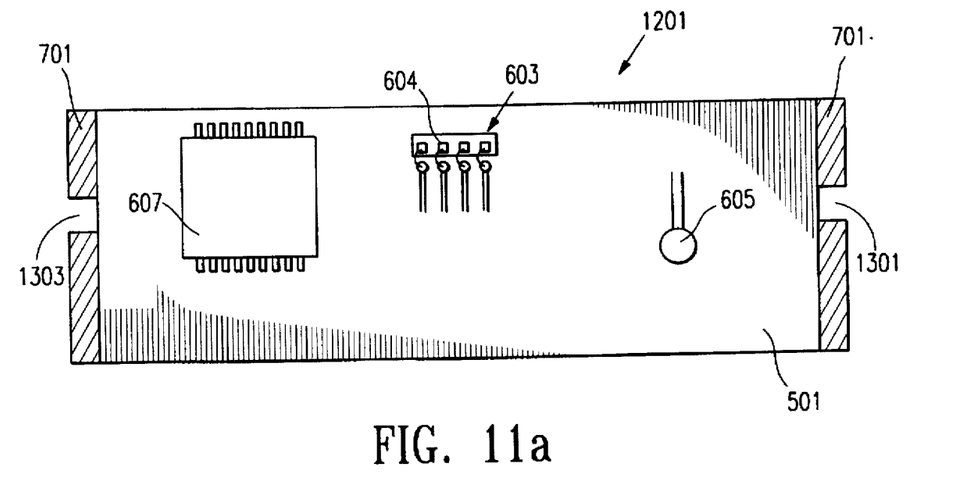
FIG. 11a is a from plan view of the potted hybrid in accordance with the preferred embodiment of the present invention.
Figure 11B:
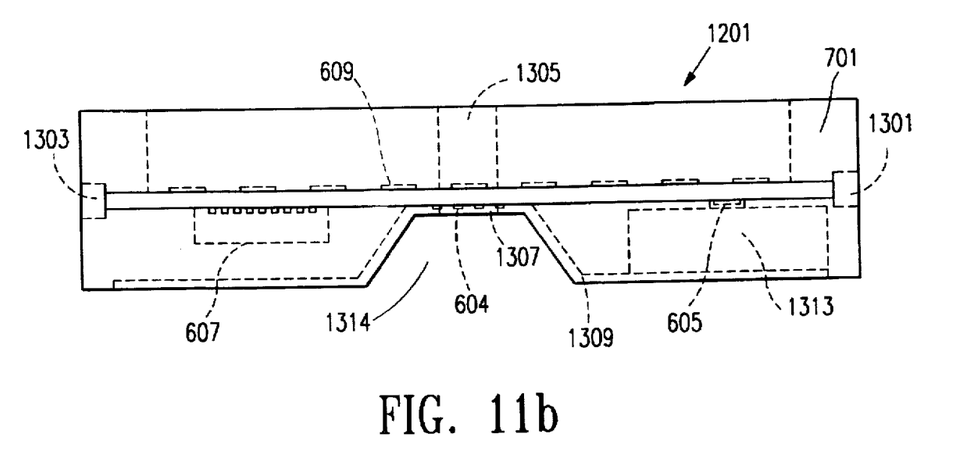
FIG. 11b is a top plan view of the potted hybrid in accordance with the preferred embodiment of the present invention.

FIG. 11a is a front plan view of the potted hybrid 1201 in accordance with the preferred embodiment of the present invention. FIG. 11b is a top plan view of the potted hybrid 1201 in accordance with the preferred embodiment oft he present invention. The potting material covers and encapsulates the sensors 603 (except for the active sensor areas 604), bonding wires (not shown) between components of the hybrid 501 and conductive traces (not shown) on the hybrid 501. Four recesses 1301, 1303, 1305, 1307 are present in the potted hybrid 1201 as a result of the protrusions 901, 902, 903, 904 which secure the hybrid within the cavity 503. In addition, a "reference well" 1313 is provided in the front side of the potted hybrid 1201. It should be clear to one of ordinary skill that the reference well 1313, and reference pad 605, may not be necessary in all embodiments of the present invention.

A flow channel 1309 is also formed to allow a solution to come into contact with the active sensor areas 604 of the sensors 603. In the preferred embodiment of the present invention, the flow channel 1309 intersects the reference well 1313 such that a solution that is present in the flow channel 1309 will be in electrical contact with a reference gel that is present within the reference well 1313. A depression 1314 is formed in the potting material that encapsulates the hybrid 501. The depression 1314 allows the flow channel 1309 to remain relatively shallow, and yet expose a solution therein to the active sensor areas 604 of the sensors 603. The flow channel exposes to the solution, the sensors, reference electrode, and any other features that it is desirable to place in contact with the solution. In embodiments such as the embodiments shown in FIGS. 7a and 7b, the flow channel must be formed above the components which extend from the hybrid substrate, but must also cause the solution that will flow through the flow channel to come into contact with those areas such as the active sensing area 604 of the sensor 603 and the reference pad 605. Preferably, the flow channel has a gentle slope which allows the fluid to flow relatively smoothly (i.e., causes minimal turbulence to the fluid flowing through the flow channel), minimizes bubble entrapment, and ensures the fluid does not stagnate within the flow channel.

Furthermore, in accordance with the present invention, the electrical contact pads 609 remain uncovered by the potting material due to the seal created by the ridge 908 (see FIG. 8) during potting. This permits electrical connections to the pads 609 after the potting process.

Figure 12:
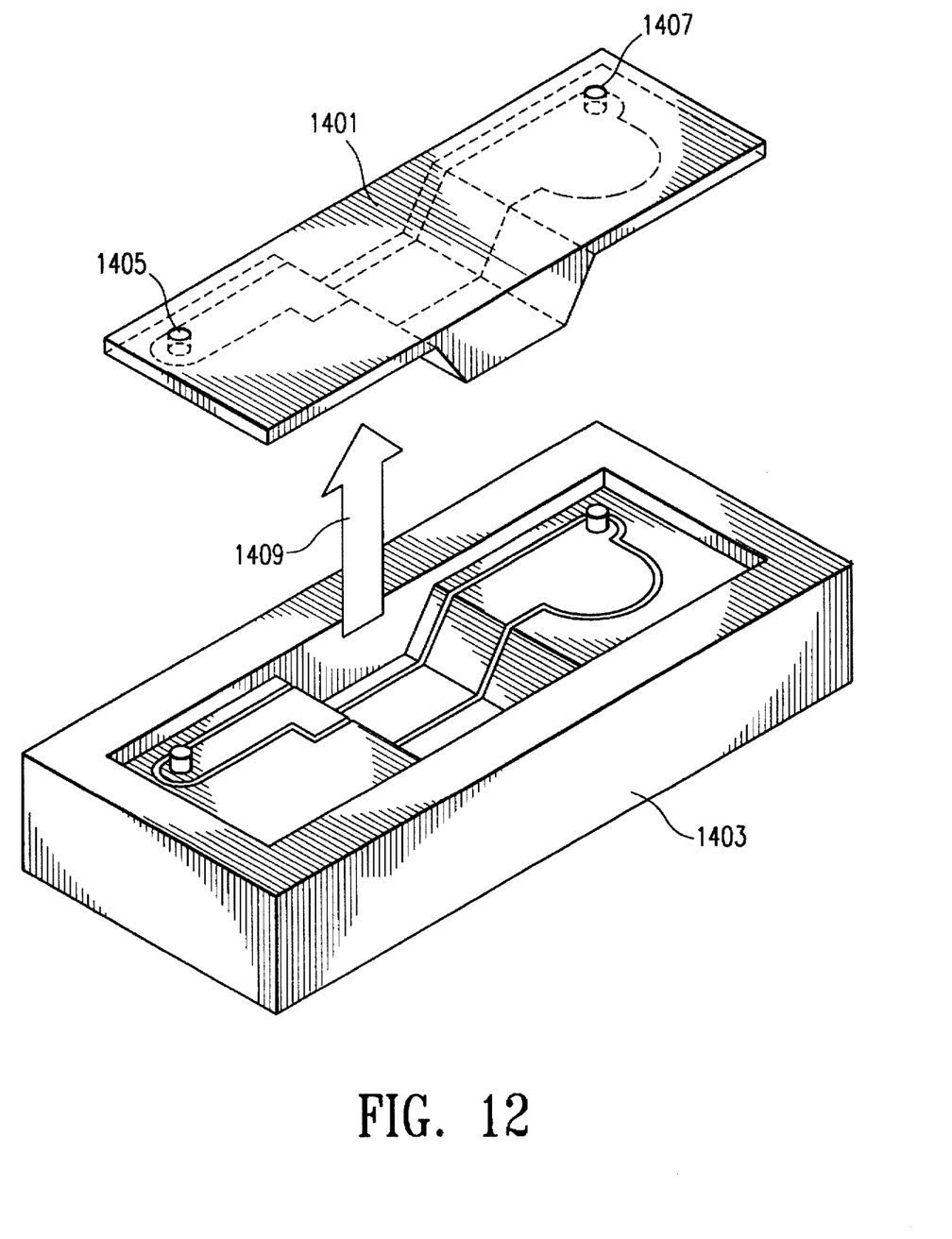
FIG. 12 is a perspective view of yet another step in the fabrication of an encapsulated sensor in accordance with the present invention.

FIG. 12 illustrates the seventh step in the fabrication of an encapsulated sensor in accordance with one embodiment of the present invention. A second tool 1403, which may be rigid or flexible, is used to fabricate a lid 1401, preferably the lid 1401 is sufficiently compressible to allow a seal to form between the lid 1401 and the potted hybrid 1201 when the lid is pressed down on the potted hybrid 1201. Alternatively, the lid may be made from the same potting material used to pot the hybrid 501. The lid 1401 has an inlet port 1405 and an outlet port 1407 to allow a solution to enter and exit the flow channel 1309. The lid 1401 is removed from the second tool 1403, as indicated by an arrow 1409 in FIG. 12.

Figure 13:
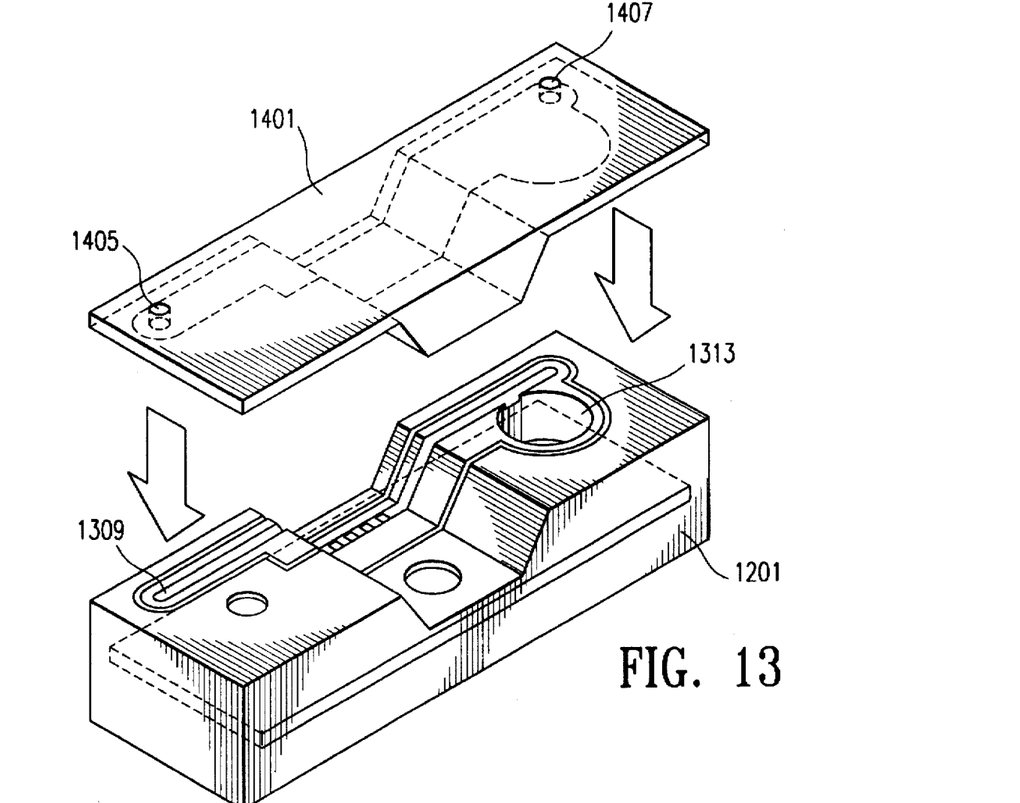
FIG. 13 and 14 are perspective views of the last step in the fabrication process in accordance with the present invention.
Figure 14:
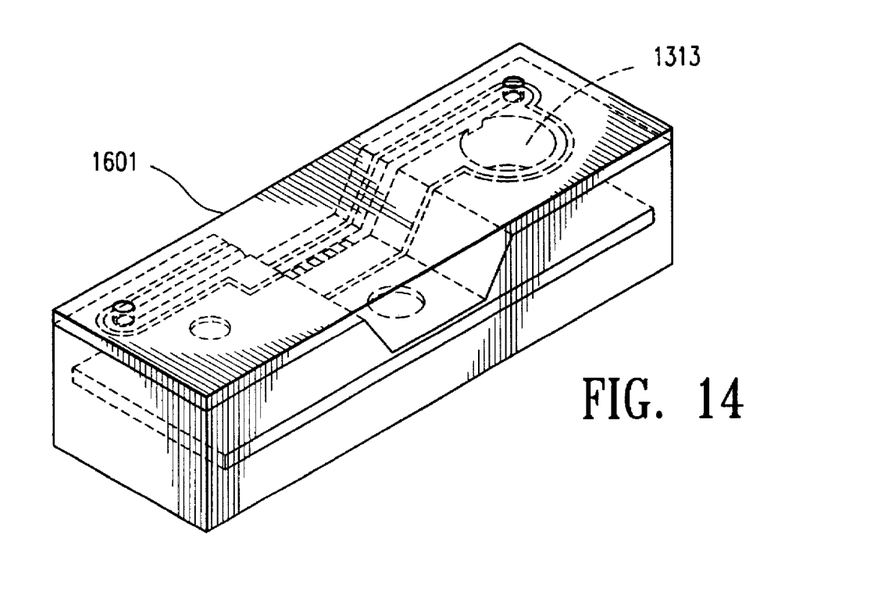

FIGS. 13 and 14 illustrate the eighth step in the fabrication process in accordance with one embodiment of the present invention. The lid 1401 is aligned with the potted hybrid 1201 such that the inlet and outlet ports 1405, 1407 are in fluid communication with the flow channel 1309. The lid 1401 is preferably sealed to the potted hybrid using an epoxy adhesive. It will be understood that any other method for sealing the lid 1401 to the potted hybrid 1201 may be used, as long as the flow channel 1309 is not blocked and the reference solution is not contaminated. For example, the lid 1401 may have a ridge which is friction fit into a matching groove in the potted hybrid 1201. Alternatively, the lid 1401 may be bound to the potted hybrid 1201 using a strap or spring which is dram tightly around the lid 1401 and potted hybrid 1201. Still further, the lid 1401 may be screwed to the potted hybrid 1201. It should be clear that numerous other methods may be employed to secure the lid 1401 to the potted hybrid 1201. In addition, in some of these embodiments, a gasket may be necessary to prevent leakage of the solution from the flow channel 1309, or the gel from the reference well 1313. The result is an encapsulated sensor 1601 having a sealed reference well 1313 and exposed electrical contact pads 609.

Figure 15:
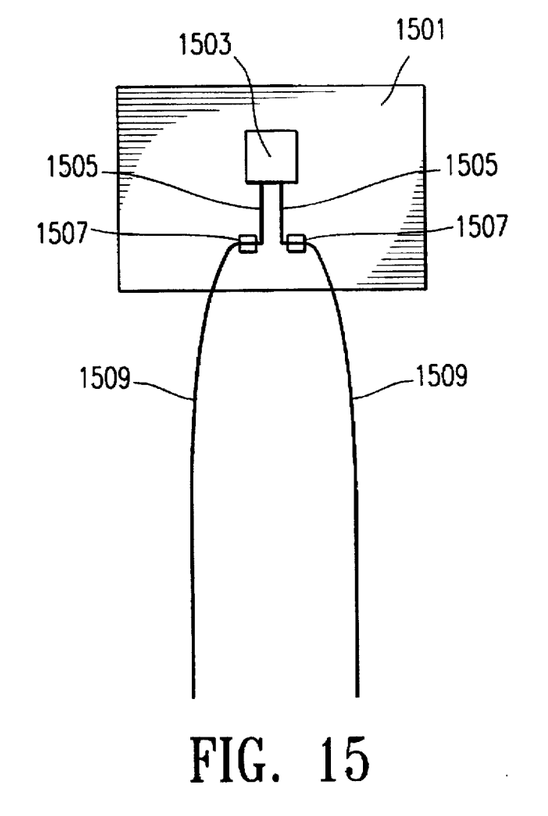
FIG. 15 is an illustration of an alternative embodiment of the present invention prior to encapsulation.
Figure 16:
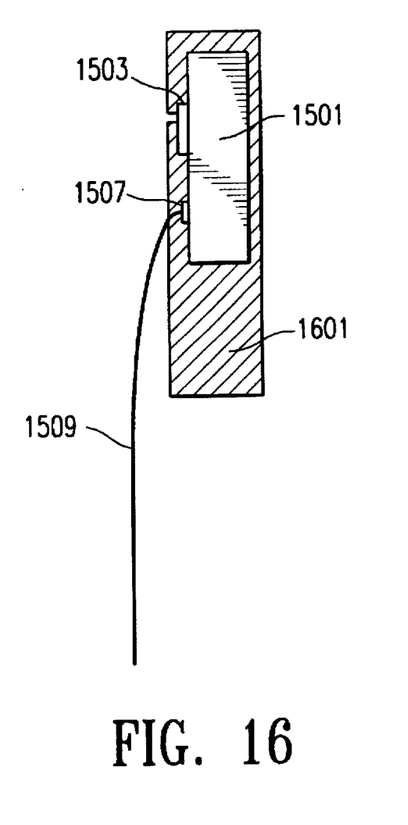
FIG. 16 is a cross-sectional view of the hybrid of FIG. 15 after encapsulation.

FIG. 15 is an illustration of an alternative embodiment of the present invention prior to encapsulation. A hybrid 1501, generally similar to the hybrid 1201, has a sensor 1503 mounted thereon. The sensor 1503 is coupled via conductors 1505, such as wire bonds or conductive traces, to conductive pads 1507. FIG. 16 is a cross-sectional view of the hybrid 1501 encapsulated in encapsulating material 1601. Wires 1509 are connected to the conductive pads 1507 and extend sufficiently away from the hybrid 1501 to ensure that the wires will protrude from the encapsulating material 1601 which is applied to encapsulate the hybrid 1501 as described above with respect to the hybrid 1201 shown in FIGS. 7a and 7b. That is, the hybrid 1501 is placed into a flexible tool similar to the tool 401 shown in FIGS. 7a and 7b. The flexible tool has at least one protrusion similar to the protrusion 904 shown in FIGS. 7b and 8 which ensures that the active sensing area of the sensor 1503 will remain exposed after encapsulation of the hybrid 1501. The embodiment shown in FIGS. 15 and 16 preferably has no reference electrode, no flow channel, and needs no lid. Only the active sensing area of the sensor 1503 and the ends of wires 1509 need be exposed after encapsulation.

Thus, by providing a flexible tool to be used as a mold for a potting a hybrid, which allows a flow channel and a reference well to be formed, and which prevents electrical contact pads from being obscured, the present invention provides an inexpensive means for mass producing encapsulated electrochemical sensors. Each of the features which are to be formed in the potting material are molded into the potting material in a single step. Because the mold used to encapsulate the hybrid in the potting material is generally flexible, a seal can be formed over areas, such as the active sensing areas of the sensors, to prevent potting material from covering those areas. Because flexible molds can be rapidly produced by an inexpensive injection molding process, the present invention makes it possible to produce large quantities of inexpensive encapsulated sensors. Furthermore, flexible molds allow "undercuts" (e.g., depressions in surfaces that are not perpendicular to the direction of motion used to separate the molded product from the mold) to be formed, while still allowing the molded product to be removed from the mold. Products having undercuts molded in a rigid mold would require the rigid mold to be destroyed in order to remove the molded product.

A number of embodiments of the present invention have been described. Nevertheless, it will be understood that various modifications may be made without departing from the spirit and scope of the invention. For example, the flexible tool 401 may be formed by any means which result in the flexible tool having the desired internal cavity 503. Furthermore, the means used to secure the position of the hybrid 501 within the flexible tool 401 may vary. For example, the substrate used to fabricate the hybrid 501 may be secured within a groove in the flexible tool such that a margin or narrow portion of one or more sides of the substrate remains unencapsulated. Still further, the flexible tool may be merely a flexible liner having generally compressible contact points at the ends of protrusions, similar to the tool described above. The flexible liner may then be placed into the inner cavity of a more rigid tool which gives the flexible tool a sufficiently stable form to allow the compressible contact points of the flexible tool to make contact with particular areas of the hybrid, in the manner described above, to cause the encapsulating material to form around the areas (such as the active sensing areas of the sensors) and thus leave such areas exposed after encapsulation. Such a flexible tool may be fabricated in more than one piece, each piece being placed into a cavity within a more rigid tool. Accordingly, it is to be understood that the invention is not to be limited by the specific illustrated embodiment, but only by the scope of the appended claims.

We claim:

1. A method for encapsulating an electrochemical sensor including the steps of:
   (a) forming a master pattern having a three-dimensional external profile and at least one depression;
   (b) fabricating an essentially flexible tool using the master pattern, the flexible tool having a cavity with a three-dimensional internal profile substantially matching the three-dimensional external profile of the master pattern, and having at least one protruding flexible structure, each flexible structure corresponding to one of the depressions on the master pattern;
   (c) placing a hybrid having at least one electrochemical sensor, and at least one contact area on the sensor, into contact with the flexible tool, such that the hybrid is supported within the cavity, and such that at least one contact area of the hybrid is in contact with at least one of the protruding flexible structures so as to seal the contact area of the hybrid to the flexible structure;
   (d) applying a potting material to the hybrid to encapsulate the electrochemical sensor; and
   (e) disengaging the encapsulated hybrid from the flexible tool, the flexible tool ensuring that each sealed contact area remains exposed after encapsulation and disengagement of the flexible tool from the hybrid.

2. A method for encapsulating an electrochemical sensor including the steps of
   (a) fabricating an essentially flexible tool having a three-dimensional cavity and at least one protruding flexible structure;
   (b) inserting a hybrid having at least one electrochemical sensor, and at least one contact area on the sensor, into the three-dimensional cavity within the flexible tool, such that the hybrid is supported within the cavity by the flexible tool, and such that the at least one contact area of the hybrid is in contact with at least one of the protruding flexible structures so as to seal the contact area of the hybrid to the flexible structure;
   (c) filling the three-dimensional cavity with a potting material to encapsulate the electrochemical sensor without encapsulating each sealed contact area of the hybrid to form an encapsulated hybrid having a depression corresponding to each protruding flexible structure;
   (d) disengaging the encapsulated hybrid from the cavity, such that each protruding flexible structure is disengaged from the corresponding depression without appreciable damage to the flexible tool.

3. A method for encapsulating an electrochemical sensor including the steps of:.
   (a) fabricating an essentially flexible tool by means of an injection molding process, the flexible tool having a cavity and at least one protruding flexible structure;
   (b) inserting a hybrid having at least one electrochemical sensor, and at least one contact area on the sensor, into the cavity within the flexible tool, such that the at least one contact area of the hybrid is in contact with at least one of the protruding flexible structures so as to seal the contact area of the hybrid to the flexible structure; and
   (c) filling the cavity with a potting material to encapsulate the electrochemical sensor without encapsulating each sealed contact area.

4. The method of claim 2, wherein the potting compound is an epoxy.

5. The method of claim 2, wherein at least one electrochemical sensor has at least one active sensing area and each active sensing area is a contact area.

6. The method of claim 2, wherein the hybrid has a reference electrode fabricated thereon and the essentially flexible tool has a protrusion for sealing the reference electrode from the potting material.

7. The method of claim 2, wherein the hybrid has a ceramic substrate.

8. The method of claim 2, wherein the hybrid has a printed circuit board substrate.

9. The method of claim 8, wherein an integrated circuit is mounted on the printed circuit board substrate.

10. The method of claim 9, wherein the integrated circuit is a programmable read only memory.

11. The method of claim 10, wherein the reference electrode is a silver pad.

12. The method of claim 10, wherein a reference well is formed in the potting material by a protrusion in the flexible tool.

13. The method of claim 1, wherein the sensor is an ISFET.

14. The method of claim 13, wherein the ISFET has a gate with a selectively permeable membrane.

15. The method of claim 1, wherein the hybrid is supported by protrusions in the flexible tool.

16. The method of claim 1, further including the steps of:
   (a) fabricating a lid; and
   (b) aligning the lid with the potted hybrid; and
   (c) sealing the lid on the potted hybrid.

17. The method of claim 16, wherein the lid has at least an inlet port and an outlet port.

18. The method of claim 1 wherein the step of using the master pattern to fabricate the essentially flexible tool is by means of an injection molding process.

19. The method of claim 2 wherein the step of fabricating the essentially flexible tool is by means of an injection molding process.

20. A method for encapsulating an electrochemical sensor, including the steps of:
   (a) forming a master pattern having a three-dimensional external profile and a plurality of depressions formed at the surface of the master pattern;
   (b) using the master pattern to fabricate an essentially flexible tool having a three-dimensional cavity with a three-dimensional internal profile substantially matching the external profile of the master pattern, the cavity including a plurality of flexible protrusions extending from the surface of the cavity, each flexible protrusion corresponding to one of the plurality of depressions on the master pattern;
   (c) placing a hybrid having a mechanical sensor and a contact area on the sensor into contact with the flexible tool, such that the hybrid is supported within the cavity by at least one of the flexible protrusions, and such that the contact area of the hybrid is in contact with at least one of the flexible protrusions so as to seal the contact area of the hybrid to the flexible structure;

(d) filling the cavity with a potting material to surround and encapsulate at least three surfaces of the hybrid without encapsulating the sealed contact area; and (e) disengaging the encapsulated hybrid from the cavity in the flexible tool, such that the plurality of flexible structures are disengaged from the corresponding depressions without appreciable damage to the flexible tool so as to allow the flexible tool to be used for encapsulating multiple hybrids.

* * * * *